United States Patent [19]

Gaides

[11] Patent Number: 5,584,300
[45] Date of Patent: Dec. 17, 1996

[54] MEASUREMENT OF LUNG AIR CAPACITY

[75] Inventor: Mark Gaides, Tel Aviv, Israel

[73] Assignee: Arocom Ltd., Holon, Israel

[21] Appl. No.: 519,013

[22] Filed: Aug. 24, 1995

[51] Int. Cl.$^6$ .................................................. A61B 5/08
[52] U.S. Cl. ........................ 128/716; 128/719; 128/725; 73/149
[58] Field of Search ........................... 128/716, 718–720, 128/724–729; 73/37.5, 38, 149

[56] References Cited

U.S. PATENT DOCUMENTS

| | | | |
|---|---|---|---|
| 5,038,773 | 8/1991 | Norlien et al. | 128/725 |
| 5,058,601 | 10/1991 | Riker | 128/725 |
| 5,207,623 | 5/1993 | Tkatchouk et al. | 128/725 |

*Primary Examiner*—Angela D. Sykes
*Assistant Examiner*—Bryan K. Yarnell
*Attorney, Agent, or Firm*—Mark M. Friedman

[57] ABSTRACT

A method for measuring the air capacity of a user's lungs. The method involves the use of an apparatus which includes a container having a constant volume and an opening adapted to allow flow communication with the lungs. The container further includes a flow sensor and a pressure sensor. The method involves determining the initial air pressure in the container before flow communication with the lungs is established. After flow communication with the lungs is established, the flows and pressures are measured. The lung air capacity is calculated based on the known constant container volume, the initial air pressure, and the changes in volume and pressure of the lungs as determined from the measured flows and pressures in the container.

7 Claims, 3 Drawing Sheets

MEASUREMENT OF LUNG AIR CAPACITY

FIELD AND BACKGROUND OF THE INVENTION

The present invention relates to method and apparatus for measuring the lung air capacity.

For a variety of diagnostic and related reasons, it is important to be able to accurately determine the volume of air in the lungs. Such measurements are crucial in evaluating lung damage as a result of disease or trauma. The measurements are also importance in analyzing the extent to which blood is accommodated in the lungs during breathing, for example under stress conditions.

Air is typically found in the lungs in two places. First, in normal lungs, virtually all the air is found in aerated portions of the lungs, i.e., in portions of the lungs from which the air can readily be expelled and replaced. A certain amount of trapped air is often found in pathological portions of the lungs, for example, in bullae, or blisters.

The air found in the aerated portions of the lungs is termed the Functional Residual Capacity (FRC) of the lungs. The total air in the lungs, including trapped air in pathological tissue, is termed Total Gas Volume (TGV).

Various techniques have been proposed for measuring lung air volume. At least two of these techniques are in common use. The gas dilution technique, described in more detail below, makes use of a spirometer which contains a certain known concentration of a gas not normally found in the lungs, such as helium. After steady state is achieved the gas is analyzed chemically and the determined concentration of the helium is used to calculate the patient's FRC.

The plethysmography technique makes use of use of a body box. The patient is placed in a body box which is hermetically sealed. The patient then breathes through a breathing tube which is then blocked and the measured pressure in the lung and breathing fluctuations of the volume of the body box are used to determine the patient's TGV.

Each of these techniques suffers from a number of disadvantages. Thus, the gas dilution technique requires the use of certain expensive and difficult to handle gases, such as helium and xenon. Furthermore, the techniques requires the use of a gas analyzer. Finally, it is not normally possible to use the technique to measure lung capacity under stress since the measurement typically takes from 3 to 7 minutes which is ordinarily longer than the time of the stress.

The biggest disadvantage of the plethysmography technique is that it requires a large and expensive body box. Here, too it is not possible to carry out the measurement under stress conditions since the body box is confining and since stress would lead to a warming of the air in the body box, thereby reducing the accuracy of the measurements. Finally, the plethysmography technique calls on the patient to simulate normal breathing but with a blocked breathing tube which is difficult for some people to accomplish, further degrading the accuracy of the technique.

There is thus a widely recognized need for, and it would be highly advantageous to have, a technique for measuring lung capacity (TGV) which is rapid and accurate, which does not require the use of bulky and expensive equipment and which can be used under various conditions, including stress, and the like.

SUMMARY OF THE INVENTION

According to the present invention, there is provided a method for measuring the air capacity of a user's lungs, comprising the steps of: (a) providing an apparatus which includes: (i) a container having a constant volume, the container having an opening adapted to allow flow communication between the container and the lungs; (ii) a flow sensor associated with the container for measuring flows related to flows through the opening; and (iii) a pressure sensor associated with the container for measuring pressures in the container; (b) determining an initial air pressure in the container when the opening of the container not in flow communication with the lungs; (c) establishing flow communication between the container and the lungs; (d) measuring flows and pressures in the container; (e) calculating lung air capacity based on the constant container volume, the initial air pressure, and changes in volume and pressure of the lungs as determined from the measured flows and pressures in the container.

Also according to the present invention, there is provided an apparatus for measuring the air capacity of a user's lungs, comprising: (a) a container having a constant volume, the container having an opening adapted to allow flow communication between the container and the lungs; (b) a flow sensor associated with the container for measuring flows related to flows through the opening; and (c) a pressure sensor associated with the container for measuring pressures in the container.

The present invention successfully addresses the shortcomings of the presently known configurations by providing a simple, rapid, highly versatile and inexpensive, yet highly accurate, technique for measuring lung air capacity.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and apparatus which can be used to measure the air lung capacity of a patient.

The principles and operation of a method and apparatus according to the present invention may be better understood with reference to the drawings and the accompanying description.

Figure 1:
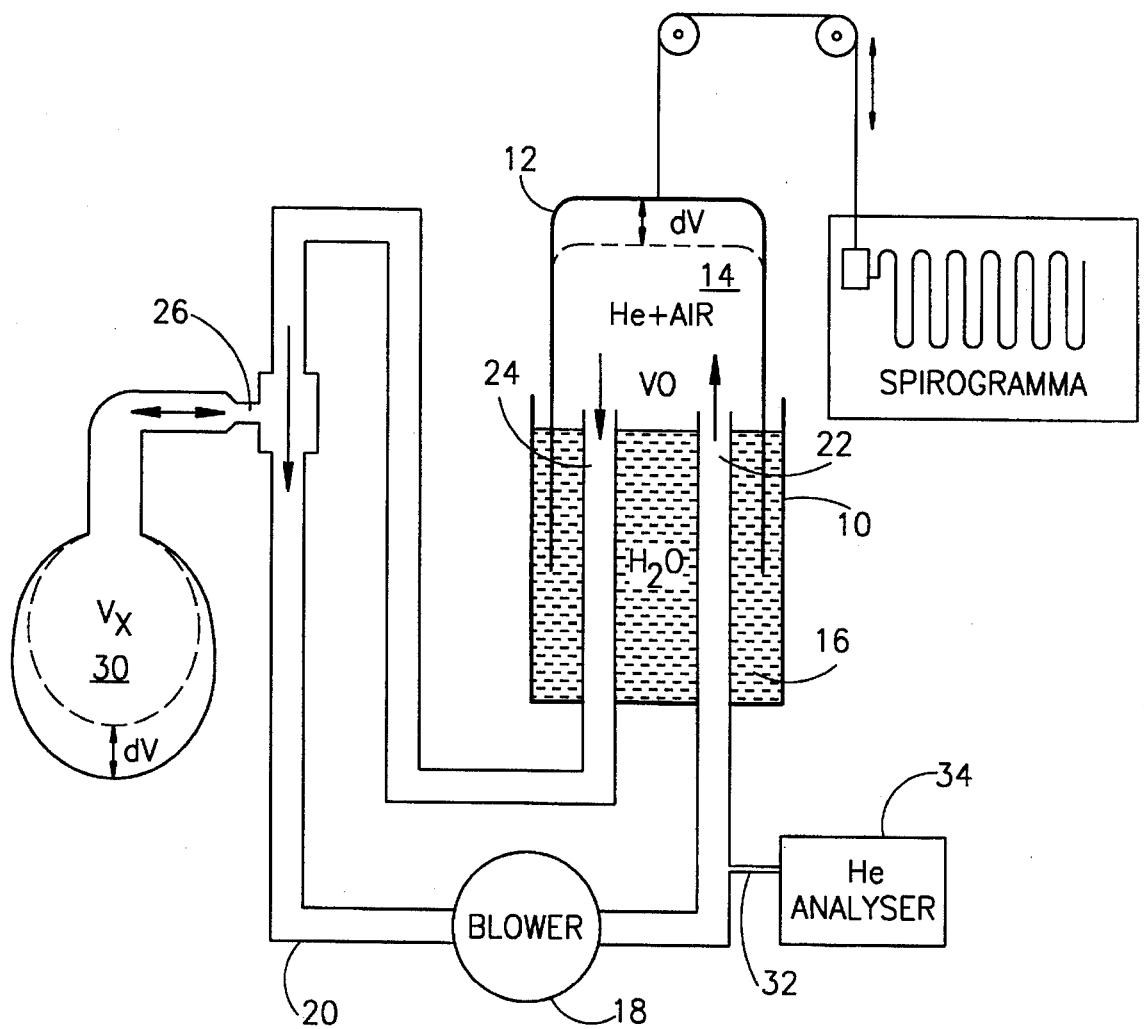
FIG. 1 schematically depicts the prior art gas dilution method of determining Functional Residual Capacity (FRC)

Referring now to the drawings, FIG. 1 illustrates the conventional gas dilution technique for measuring Functional Residual Capacity (FRC). The technique makes use of a spirometer 10 which includes a roof member 12 which rises and falls as air is introduced into and withdrawn from the gas space 14. Gas space 14 is typically defined by the impermeable walls of roof member 12 and a liquid seal, typically water 16.

Gas is circulated through pipe 20 gas space 14 using a suitable blower 18. Pipe 20 has an outlet 22 into gas space 14 and an inlet 24 from gas space 14. Pipe 20 has a further lung inlet 26 in flow communication with the lungs 30 of the patient, typically through a suitable connector (not shown) such as mouthpiece or a nose/mouthpiece, i.e., a device designed to fit over both the mouth and nose of the patient. Pipe 20 has a further analyzer outlet 32 for sampling the gas in pipe 20 and directing a portion of the gas to a gas analyzer 34 for analysis.

The gas dilution technique operates as follows. Prior to establishing flow communication between the spirometer and the lungs, the spirometer is filled with a gas which includes a known concentration of a gas which is not normally found in the lungs, such as xenon or helium. For purposes of exposition, it is assumed that the gas is helium. Flow communication between the lungs and the spirometer is then established through lung inlet 26 and the patient proceeds to breath normally but exclusively through lung inlet 26 for a relatively extended period of time, typically from about 3 to about 7 minutes. As the patient breathes, he draws air and helium from the spirometer. The breathing over several minutes causes the equalization of helium concentration (steady state) in both the spirometer and the lungs, i.e., the helium concentration becomes uniform throughout both the spirometer and the lungs. The concentration of helium is then measured by gas analyzer 34 and the result is used to calculate the patient's FRC.

This can be accomplished by carrying out a helium balance before and after connection of the spirometer to the patient's lungs. Thus,

| helium before connection to patient's lungs | = | helium after connection to patient's lungs |
|---|---|---| hence, $V_o a = V_o b + V_x b$ or, $V_o(a-b) = V_x b$ finally, the desired volume is given by, $V_x = V_o[(a-b)/b]$ where, $V_x$ is the volume (FRC) of the lungs $V_o$ is the total volume of the spirograph (including piping)

a is the starting concentration of He b is the final concentration of He

Figure 2A:
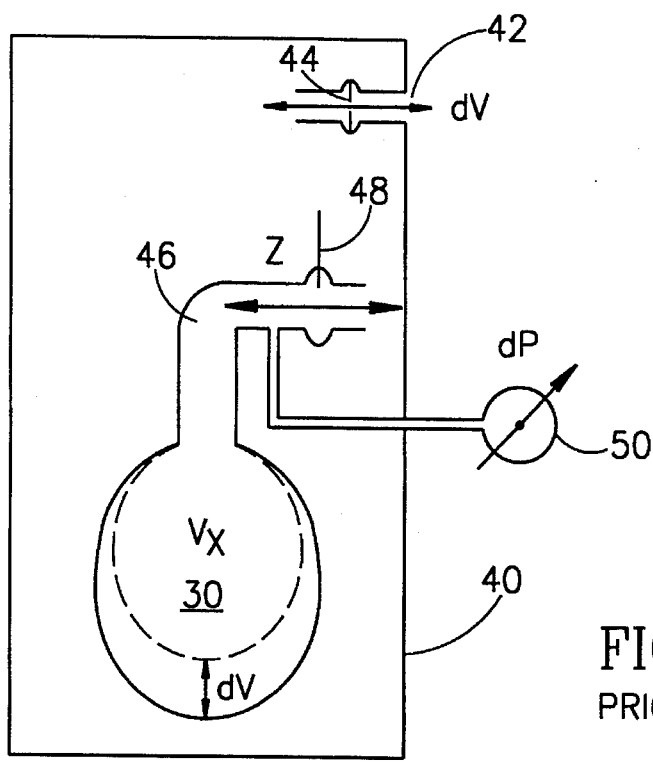
FIGS. 2a and 2b schematically depict the prior art plethysmography method of determining Total Gas Volume (TGV) showing the situation during normal breathing (FIG. 2a) and during measurement (FIG. 2b)
Figure 2B:
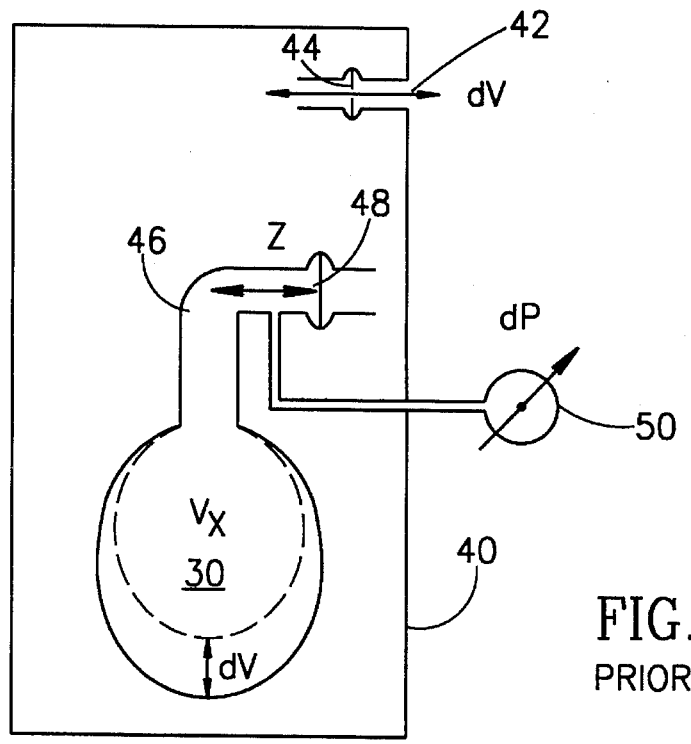

The second widely used technique, plethysmography, is illustrated during two phases of operations in FIGS. 2a and 2b.

The plethysmography technique makes use of use of a hermetically sealed body box 40 into which the entire patient is placed. Body box 40 includes a single opening 42 to the outside. A flow sensor, or meter, 44 measures the flows across opening 42. The patient is provided with a suitable breathing tube 46 which may be a mouthpiece (with nose plugged) or a nose/mouthpiece. Breathing tube 46 is equipped with a suitable valve 48 which is capable of alternately permitting and blocking the passage of air through breathing tube 46. Located between valve 48 and the patient's lungs is a pressure sensor, or meter, 50 for measuring the pressure in the patient's lungs.

The plethysmography technique operates as follows. After placing the patient in body box 40 the patient breathes freely through breathing tube 46 with valve 48 in the open position (FIG. 2a). At some point, valve 48 is closed and the patient is instructed to continue 'breathing' just as he had been doing prior to the closing of valve 48. In other words, the patient is instructed to exert the same forces in an effort to exhale as he did before valve 48 was closed making actual exhalation impossible. Because exhalation is no longer possible, the effort to exhale results in an increase in the patient's total volume as the chest cavity and stomach cavity enlarge in an effort to expel the air from the lungs. The increase volume of the patient results in flow of gas from body box 40 through opening 42 which is measured by flow sensor 44. In addition, the efforts by patient to expel air from his lungs results in an increased pressure in the lungs which is measured by pressure sensor 50. The measured data is then used to calculate the patient's TGV.

This can be accomplished by assuming the air in the patient's lungs behaves as an ideal gas so that PV/T= constant and further assuming that the temperature of the air before and after the closing of the valve is the same. Thus,

| (pressure in lungs × lung volume)$_{free\ breathing}$ | = | (pressure in lungs × lung volume)$_{blocked\ breathing}$ |
|---|---|---|

Figure 3:
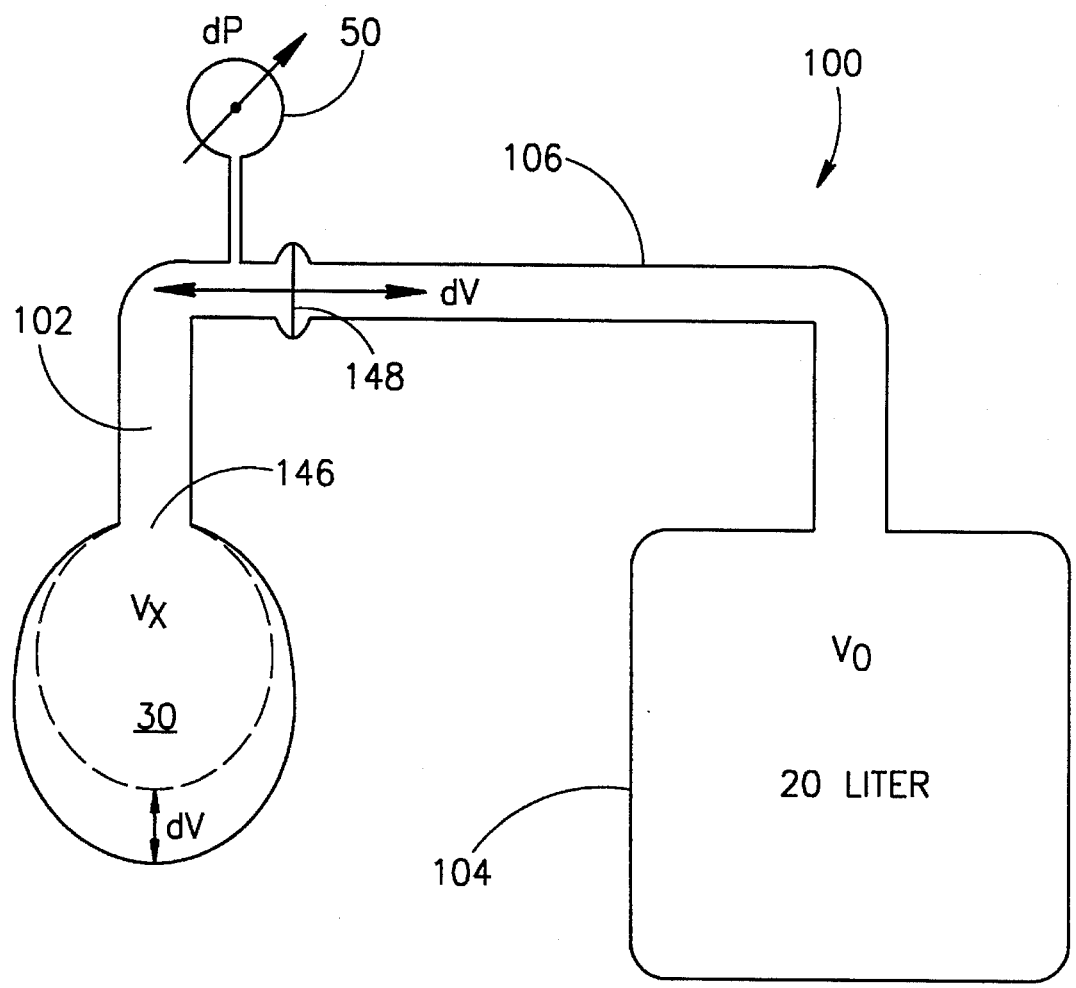
FIG. 3 schematically depicts the method according to the present invention of determining Total Gas Volume (TGV).

Hence, $P_o V_x = (P_o + dP)(V_x + dV)$ or, $P_o V_x = P_o V_x + V_x dP + P_o dV + dPdV$ so, $V_x dP = -(P_o + dP)dV$ finally, the desired volume is given by, $V_x = -(P_o + dP)(dV/dP)$ where, $V_x$ is the volume (TGV) of the lungs $P_o$ is the starting lung pressure during free breathing dV is the change in volume of the lungs upon blocking breathing dP is the change in pressure of the lungs upon blocking breathing As outlined above, the gas dilution and plethysmography techniques suffer from a number of serious disadvantages. These disadvantages may be readily overcome using the method and apparatus of the present invention which is depicted schematically in FIG. 3.

An apparatus according to the present invention includes a container 100 having a constant volume which is known. The requirement for a constant, i.e., unchanging, volume, can readily be made by constructing the various portions of container 100 of a rigid material which will not flex under normal operating pressure differences.

Container 100 includes an opening 102 which adapted to allow flow communication between container 100 and lungs 30. Preferably, container 100 includes an enlarged relatively high capacity (e.g., 20 liter) storage section 104 and a tubular section 106 which features opening 102 at its far end.

The apparatus further includes flow sensor, or meter, 148 which is associated with container 100, preferably installed in tubular section 106 of container 100. Flow sensor 148 is used to measure flows related to flows through opening 102.

Finally, the apparatus includes pressure sensor, or meter, 50 which is associated with container 100, preferably installed in tubular section 106 of container 100. Pressure sensor 50 is used to measure pressures in the system which includes container 100 and lungs 30.

In operation, a method and apparatus according to the present invention works as follows. A measurement is taken of the pressure in container 100 prior to establishing flow communication with lungs 30 or at any other convenient starting point. Flow communications is then established between container 100 and lungs 30 through a suitable breathing tube 146 which may be a mouthpiece (with nose of the patient plugged) or which may be a nose/mouthpiece, i.e., a device which fits over both the mouth and nose of the patient.

As the patient breathes normally flow sensor 148 and pressure sensor 50 continuously measure the flows and pressures. These measurements, along with the constant container volume and the initial air pressure, can then be used to calculate the patient's lung air capacity (TGV).

This can be accomplished by assuming the air in the patient's lungs behaves as an ideal gas so that PV/T= constant and further assuming that the temperature of the air before and after the closing of the valve is the same. Thus, (pressure in lungs & container × lung & container volume)$_{initial}$ = (pressure in lungs & container × lung & container volume)$_{final}$ Hence, $$P_o(V_x+V_o)=(P_o+dP)(V_x+V_o+dV)$$

so, $$P_oV_x+P_oV_o=P_oV_x+P_oV_o+P_odV+V_xdP+V_odP+dPdV$$

i.e., $$V_xdP=-V_odP-(P_o+dP)dV$$

finally, the desired volume is given by, $$V_x=-[V_o+dV(1+P_o/dP)]$$

where, $V_x$ is the volume (TGV) of the lungs
$V_o$ is the constant volume of the container
$P_o$ is the starting pressure
dV is the change in volume of the lungs
dP is the change in pressure of the lungs The lung capacity determinations may be made from the beginning to the end of one or more inhalations and/or from the beginning to the end of one or more exhalations. Preferably, the determination is made from the beginning to the end of one or more inhalation. This is because during exhalation the abdominal muscles apply pressure to the stomach and surrounding organs which contain air. Hence, during exhalation the air in the stomach and other organs is included in the TGV, thereby reducing the accuracy of the measurement. By contrast, during inhalation essentially only air found in the lungs is affected, resulting in a highly accurate TGV determination.

While the invention has been described with respect to a limited number of embodiments, it will be appreciated that many variations, modifications and other applications of the invention may be made, all of which are intended to be included within the scope of the present invention.

What is claimed is:

1. An apparatus for measuring an air capacity of a user's lungs, comprising:

(a) a constant-volume container, said constant-volume container having a tubular member for detachably attaching said constant-volume container to a user's lungs, said tubular member having an opening for allowing flow communication between said constant-volume container and the lungs, said constant-volume container and the lungs defining a closed system having a volume;

(b) a flow sensor associated with said constant-volume container for measuring flows related to volume changes in said closed system; and, (c) a pressure sensor associated with said constant-volume container for measuring an initial pressure and pressure changes in said closed system, said initial pressure, pressure changes and volume changes in said closed system and the volume of said constant-volume container being indicative of the air capacity of the lungs.

2. The apparatus of claim 1, wherein said container is rigid.

3. The apparatus of claim 1, wherein said flow sensor is a flow meter.

4. The apparatus of claim 1, wherein said opening is equipped with a mouthpiece.

5. The apparatus of claim 1, wherein said opening is equipped with a mask adapted to cover the nose and mouth of a user.

6. A method for measuring an air capacity of a user's lungs, comprising the steps of:

(a) providing an apparatus which includes:

(i) a constant-volume container, said constant-volume container having a tubular member for detachably attaching said constant-volume container to a user's lungs, said tubular member having an opening for allowing flow communication between said constant-volume container and the lungs, said constant-volume container and the lungs defining a closed system having a volume;

(ii) a flow sensor associated with said constant-volume container for measuring flows related to volume changes in said closed system; and, (iii) a pressure sensor associated with said constant-volume container for measuring an initial pressure and pressure changes in said closed system;

(b) determining an initial air pressure in said closed system;

(c) measuring volume changes and pressure changes in said closed system; and, (d) calculating the air capacity of the lungs according to:

$$V_x=-[V_o+dV(1+P_o/dP)]$$

where, $V_x$ is the air capacity of the lungs
    $V_o$ is the volume of said constant-volume container
    $P_o$ is the initial air pressure in said closed system
    dV is the volume change of said closed system
    dP is the pressure change in said closed system.

7. The method of claim 6, wherein said initial air pressure is measured before the establishment of flow communication between said constant-volume container and the lungs.

* * * * *